(12) United States Patent
Lee et al.

(10) Patent No.: US 9,322,751 B2
(45) Date of Patent: Apr. 26, 2016

(54) AEROSOL COLLECTING DEVICE

(71) Applicants: Jonghee Lee, Daejeon (KR); Young-Su Jeong, Daejeon (KR); Sun Kyung Choi, Sejong-si (KR); Ju Hyun Kim, Seongnam-si (KR)

(72) Inventors: Jonghee Lee, Daejeon (KR); Young-Su Jeong, Daejeon (KR); Sun Kyung Choi, Sejong-si (KR); Ju Hyun Kim, Seongnam-si (KR)

(73) Assignee: AGENGY FOR DEFENSE DEVELOPMENT, Daejeon (KR)

( * ) Notice: Subject to any disclaimer, the term of this patent is extended or adjusted under 35 U.S.C. 154(b) by 243 days.

(21) Appl. No.: 14/097,439

(22) Filed: Dec. 5, 2013

(65) Prior Publication Data
US 2015/0059497 A1 Mar. 5, 2015

(30) Foreign Application Priority Data
Sep. 2, 2013 (KR) .................. 10-2013-0104872

(51) Int. Cl.
*G01N 1/24* (2006.01)
*G01N 1/22* (2006.01)
*G01N 1/02* (2006.01)

(52) U.S. Cl.
CPC .............. *G01N 1/24* (2013.01); *G01N 1/2208* (2013.01); *G01N 2001/022* (2013.01)

(58) Field of Classification Search
USPC ..................................... 73/863.22
See application file for complete search history.

(56) References Cited

U.S. PATENT DOCUMENTS

| 2005/0072218 A1* | 4/2005 | Iwata | G01N 30/84 73/61.54 |
| 2005/0126260 A1* | 6/2005 | Totoki | B01D 49/00 73/31.02 |
| 2008/0229930 A1* | 9/2008 | Jordan | B01D 45/10 96/413 |
| 2011/0167931 A1* | 7/2011 | Vellutato, Jr. | G01N 33/497 73/863.11 |

FOREIGN PATENT DOCUMENTS

| KR | 20110102064 A | 9/2011 |
| KR | 20130047632 A | 5/2013 |
| KR | 20130050035 A | 5/2013 |
| KR | 20130080339 A | 7/2013 |

* cited by examiner

*Primary Examiner* — Hezron E Williams
*Assistant Examiner* — Mark A Shabman
(74) *Attorney, Agent, or Firm* — Scully Scott Murphy and Presser; Edward Grolz

(57) ABSTRACT

An aerosol collecting device includes: a sample plate; and a housing having a sample passing space around the sample plate so as to enclose at least part of the sample plate, wherein the housing includes: a first body having a sample inlet on one surface thereof; and a second body having a suction opening on one surface thereof, the suction opening configured to suck air inside the sample passing space, the second body formed to be engaged with the first body in a state where the sample plate is interposed therebetween.

12 Claims, 10 Drawing Sheets

AEROSOL COLLECTING DEVICE

CROSS-REFERENCE TO RELATED APPLICATION

Pursuant to 35 U.S.C. §119(a), this application claims the benefit of earlier filing date and right of priority to Korean Application No. 10-2013-0104872, filed on Sep. 2, 2013, the contents of which is incorporated by reference herein in its entirety.

BACKGROUND OF THE DISCLOSURE

1. Field of the Disclosure

The present disclosure relates to an aerosol collector, and more particularly, an aerosol collecting device capable of collecting aerosol particles floating in the air.

2. Background of the Disclosure

In the field of a biological warfare and a biological terror, an attack method for damaging the human body by infection through a respiratory organ is mainly used. To this end, an attacker sprays biological agents or harmful materials in the air in the form of aerosol. In order to effectively react to such attack, the harmful materials should be early detected and components of the harmful materials should be identified.

Recently, a method for detecting and identifying biological harmful materials using MALDI-TOF (Matrix Assisted Laser Desorption and Ionization Time-Of-Flight) mass spectrometer have been spotlighted. Unlike other mass spectrometers, the MALDI-TOF mass spectrometer can perform a mass analysis in a wide band (several kD~several hundred kD). Therefore, the MALDI-TOF mass spectrometer can easily analyze a mass of biological particles, a type of a polymer compound. Further, it takes a much shorter time (less than 1 second) for the MALDI-TOF mass spectrometer to analyze a sample than other mass spectrometers. Therefore, the MALDI-TOF mass spectrometer can serve to early determine harmful materials.

A sample analysis method by the MALDI-TOF mass spectrometer is as follows.

Firstly, a sample to be analyzed is mixed with a matrix, and then is ionized using energy of a pulse laser. Then, the ionized sample is accelerated in a strong electric field, so that a Time-Of-Flight of the sample can be measured according to a mass. Then, a mass spectrum of the sample is formed based on the measured result. Once the formed mass spectrum is analyzed, components of the sample can be identified. Accordingly, whether a biological attack has occurred or not can be determined.

However, in case of determining whether a biological attack has occurred or not using such mass spectrometry, the following problems may be caused.

Firstly, the MALDI-TOF mass spectrometry cannot collect samples real time on the battlefield, despite advantages that a wide range of masses can be analyzed, and a sample analysis can be performed more quickly than other mass spectrometry.

A sample to be detected using such mass spectrometry is aerosol type biological particles floating in the air. It is not easy to directly drop such aerosol type biological particles, on a sample plate of the MALDI-TOF mass spectrometer. In the conventional art, particles in the air was collected using an impinger. Then, the collected particles were separated from each other (concentrated) by a centrifugal process. Then, the concentrated sample is suspended using purified water. Then, the suspension was dropped onto a dropping spot of the sample plate using a pipette. Such processes are performed manually for 10 minutes or more.

In order to early detect a biological warfare and a biological terror on the battlefield, required is a technique capable of collecting aerosols flowing in the air, and then capable of directly absorbing samples onto the sample plate of the MALDI-TOF mass spectrometer, without extracting the samples using the collected biological particles (bioaerosols).

SUMMARY OF THE DISCLOSURE

Therefore, an aspect of the detailed description is to provide an aerosol collecting device capable of absorbing bioaerosols floating in the air onto a sample plate in an analyzable manner.

To achieve these and other advantages and in accordance with the purpose of this specification, as embodied and broadly described herein, there is provided an aerosol collecting device, comprising: a sample plate; and a housing having a sample passing space around the sample plate so as to enclose at least part of the sample plate, wherein the housing includes a first body having a sample inlet on one surface thereof, and a second body having a suction opening on one surface thereof, the suction opening configured to suck air inside the sample passing space, the second body formed to be engaged with the first body in a state where the sample plate is interposed therebetween.

In an embodiment of the present invention, the sample inlet and the suction opening may be disposed to face each other.

In another embodiment of the present invention, the first body may include: a first surface including the sample inlet; and a second surface extending from one end of the first surface in a thickness direction of the housing, and having a groove on one end thereof, the groove formed to have a shape corresponding to the sample plate.

In another embodiment of the present invention, the second body may include: a third surface including the suction opening; and a fourth surface extending from one end of the third surface in a thickness direction of the housing, and having a groove on one end thereof, the groove formed to have a shape corresponding to the sample plate.

In another embodiment of the present invention, the housing may include a contact member mounted to the housing so as to be adhered to an interface between the housing and the sample plate.

In another embodiment of the present invention, the contact member may include a first member attached to an inner surface of the first body; and a second member attached to an inner surface of the second body, and configured to seal the sample passing space by contacting the first member.

In another embodiment of the present invention, the first member may include a first hole covering an inner surface of the first body and overlapping the sample inlet, and the second member may include a second hole covering an inner surface of the second body and overlapping a suction opening.

In another embodiment of the present invention, the first member may include a first central portion spaced from the sample plate to form a sample passing space; and a first edge portion enclosing the first central portion, and formed to be engaged with the second member.

In another embodiment of the present invention, the second member may include a second central portion spaced from the sample plate to form a sample passing space; and a second edge portion enclosing the second central portion, and formed to be engaged with the first edge portion.

In another embodiment of the present invention, the first edge portion may include a first region contacting the sample plate; and a second region contacting the second edge portion.

In another embodiment of the present invention, the sample passing space may be formed between the second region and the sample plate.

In another embodiment of the present invention, the housing may include a first connection member protruding from the first body to thus have a prolonged length, the first connection member including a flow path for connecting the sample inlet to outside.

In another embodiment of the present invention, a concaved surface may be formed at an inner surface of the first body.

In another embodiment of the present invention, the sample inlet may include a plurality of holes connected from an outer surface of the first body to the concaved surface.

In another embodiment of the present invention, the sample plate may be a sample plate of MALDI-TOF (Matrix Assisted Laser Desorption and Ionization Time-Of-Flight) mass spectrometer.

In another embodiment of the present invention, the aerosol collecting device may further include a pressure controller connected to the suction opening, and configured to control a pressure inside the sample passing space.

In another embodiment of the present invention, the housing may be formed to have a length shorter than that of the sample plate.

In another embodiment of the present invention, the housing may include a transparent window through which the sample plate is viewed from outside.

The aerosol collecting device according to the present invention can have the following advantages.

Firstly, as bioaerosols floating in the air are directly absorbed into the MALDI-TOF sample plate, a concentrating process and a dropping process can be omitted from sample processing procedures. Under such configuration, whether a biological attack has occurred on the battlefield or not can be determined for the military purpose in a simple and rapid manner. Further, a function to detect contaminants in the air and an alarm function using such device can be enhanced for the general purpose.

Further scope of applicability of the present application will become more apparent from the detailed description given hereinafter. However, it should be understood that the detailed description and specific examples, while indicating preferred embodiments of the disclosure, are given by way of illustration only, since various changes and modifications within the spirit and scope of the disclosure will become apparent to those skilled in the art from the detailed description.

BRIEF DESCRIPTION OF THE DRAWINGS

The accompanying drawings, which are included to provide a further understanding of the disclosure and are incorporated in and constitute a part of this specification, illustrate exemplary embodiments and together with the description serve to explain the principles of the disclosure.

In the drawings.

DETAILED DESCRIPTION OF THE DISCLOSURE

Description will now be given in detail of the exemplary embodiments, with reference to the accompanying drawings. For the sake of brief description with reference to the drawings, the same or equivalent components will be provided with the same reference numbers, and description thereof will not be repeated.

Though terms of 'first', 'second', etc. are used to explain various components, the components are not limited to the terms. The terms are used only to distinguish one component from another component. For example, a first component may be referred to as a second component, or similarly, the second component may be referred to as the first component within the scope of the present invention.

When it is mentioned that one component is "connected" or "accessed" to another component, it may be understood that the one component is directly connected or accessed to the another component or that still other component is interposed between the two components. In the meantime, when it is mentioned that one component is "directly connected" or "directly accessed" to another component, it may be understood that no component is interposed therebetween.

Figure 1:
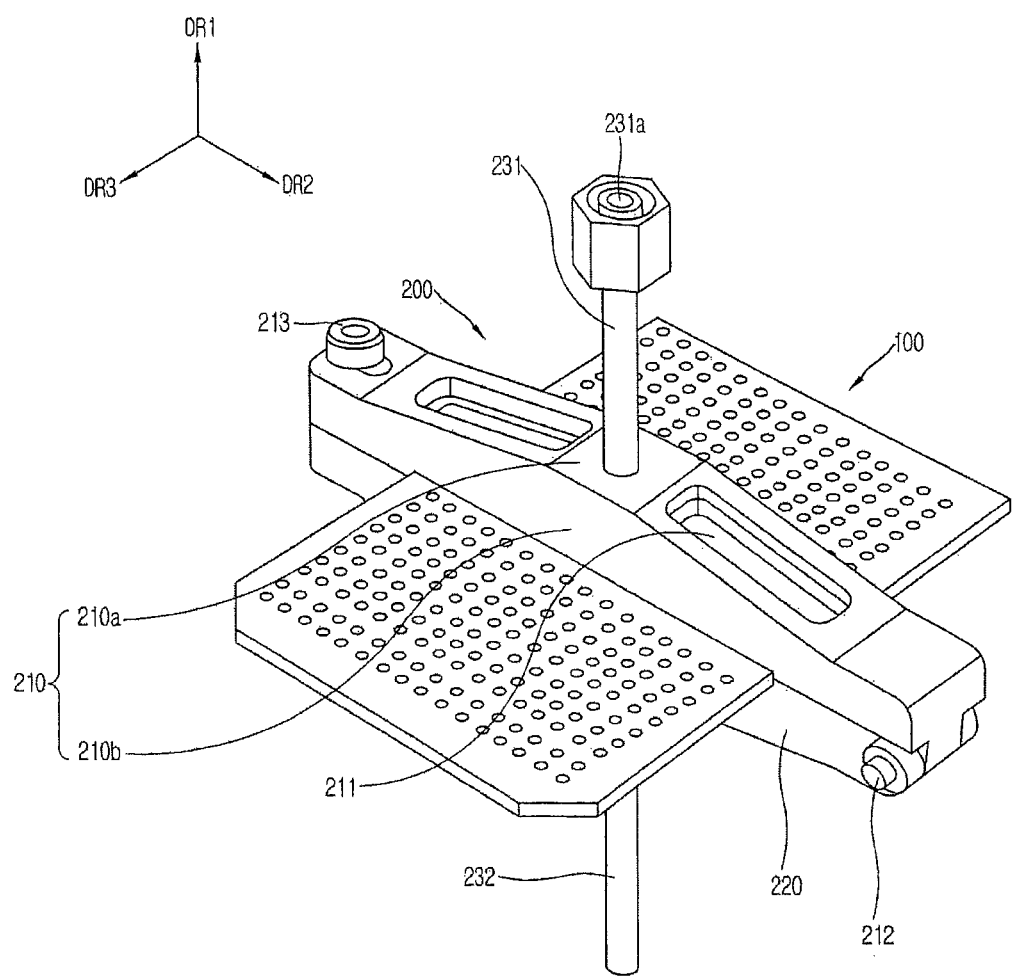
FIG. 1 is a perspective view of an aerosol collecting device according to an embodiment of the present invention.

FIG. 1 is a perspective view of an aerosol collecting device 200 according to an embodiment of the present invention, and FIG. is a sectional view of the aerosol collecting device 200 of FIG. 1.

Figure 2:
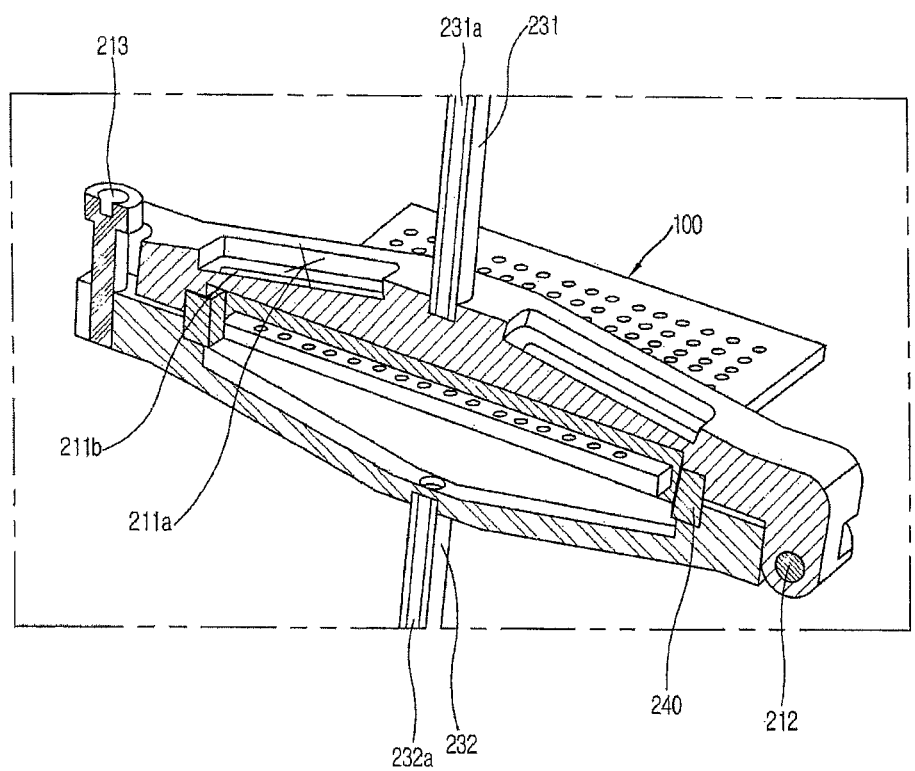
FIG. 2 is a sectional view of the aerosol collecting device of FIG. 1.

Referring to FIGS. 1 and 2, the aerosol collecting device 200 includes a sample plate 100 and a housing. The aerosol collecting device 200 according to an embodiment of the present invention is configured to collect samples for MALDI-TOF (Matrix Assisted Laser Desorption and Ionization Time-Of-Flight) mass spectrometry. That is, as the sample plate 100 coupled to the housing, a sample plate for MALDI-TOF mass spectrometry can be used.

The housing includes a first body 210 and a second body 220.

The first body 210 is formed to cover an upper surface of the sample plate 100. More specifically, the first body 210 is formed to overlap one row of dropping region on an upper surface of the sample plate 100. The first body 210 may include a first surface 210a including a sample inlet, and a second surface 210b extending from one end of the first surface 210a in a thickness direction of the housing.

The first surface 210a and the second surface 210b are categorized for convenience, which are included in embodiments of the present invention even if a boundary between the first surface 210a and the second surface 210b is not clear. That is, the second surface 210b may mean part of the first surface 210a extending to a thickness direction of the housing.

The thickness direction of the housing indicates an up and down direction (DR 1) of the aerosol collecting device 200 shown in FIG. 1. For reference, a width direction indicates a right and left direction (DR 2), and a length direction indicates a back and forth direction (DR 3).

The housing may further include a first connection member 231 protruding from the first body 210 to thus have a prolonged length. The first connection member 231 includes a flow path 231*a* for connecting the sample inlet of the first surface 210*a* to outside.

The first body 210 includes an observation module 211. As shown in FIG. 2, the observation module 211 includes a transparent window 211*b*, and a groove 211*a* for mounting the transparent window 211*b*.

The second body 220 is formed to cover a lower surface of the sample plate 100. The second body 220 includes a third surface including a suction opening, and a fourth surface 220*b* extending from one end of the third surface in a thickness direction of the housing. The third surface and the fourth surface 220*b* are categorized for convenience, which are included in embodiments of the present invention even if a boundary between the third surface and the fourth surface 220*b* is not clear. That is, the fourth surface 220*b* may mean part of the third surface extending to a thickness direction of the housing.

The housing may further include a second connection member 232 protruding from the second body 220 to thus have a prolonged length. The second connection member 232 includes a flow path 232*a* for connecting the suction opening of the third surface to outside.

A fixing pin 212 is coupled to one end of the first body 210 and the second body 220. The fixing pin 212 serves as a hinge through which the first body 210 and the second body 220 perform a relative motion.

A bolt 213 is coupled to another end of the first body 210 and the second body 220. The bolt 213 allows the first body 210 and the second body 220 to maintain a closed state when engaged with each other.

In an embodiment of the present invention, when the housing is in a closed state (i.e., when the first body and the second body are engaged with each other), the sample inlet and the suction opening are disposed to face each other. That is, the sample inlet is formed at a central part of the first surface 210*a*, and the suction opening is formed at a central part of the third surface. The suction opening is formed to be symmetrical to the sample inlet in a state where the sample plate 100 is interposed therebetween. Under such configuration, if air inside the sample passing space is sucked through the suction opening, introduced aerosols are uniformly dispersed to two sides of the sample plate 100.

A contact member 240 is mounted in the housing. The contact member 240 forms a sample passing space around the sample plate 100. Air introduced into the aerosol collecting device 200 through the sample inlet is discharged to the suction opening via the sample passing space.

Figure 3:
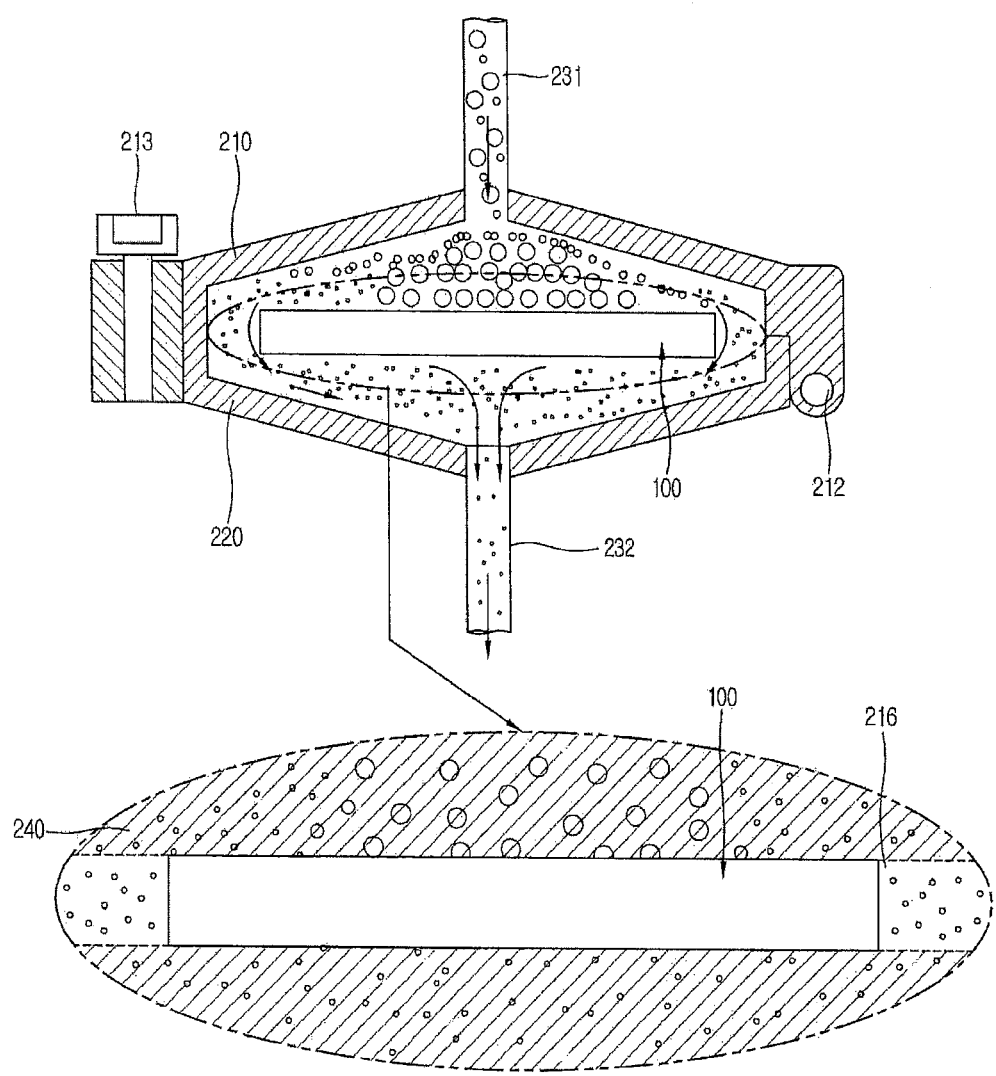
FIG. 3 is a conceptual view illustrating an operation of the aerosol collecting device of FIG. 1.

FIG. 3 is a conceptual view illustrating an operation of the aerosol collecting device 200 of FIG. 1.

Referring to FIG. 3, air introduced into the aerosol collecting device 200 includes bioaerosols of various sizes and masses.

As shown in FIG. 3, air introduced into the aerosol collecting device 200 flows along the sample passing space around the sample plate 100. Then, the air is discharged to the suction opening. The flowing direction of the air is indicated by the arrows.

A pressure controller, configured to control a pressure inside the sample passing space, may be connected to the suction opening. If an inner pressure of the aerosol collecting device 200 is lower than an atmospheric pressure, air is introduced into the aerosol collecting device 200 through the sample inlet. Aerosol particles in the air collide with an upper surface of the sample plate 100 due to inertia. Massive particles collide with the sample plate 100 to thus be absorbed onto the surface of the sample plate 100. On the other hand, light particles are introduced into the second body 220 through the sample passing space disposed at two sides of the sample plate 100, along a flowing direction of air. Then, the light particles are discharged to the suction opening.

In an embodiment of the present invention, the sample inlet and the suction opening are disposed to overlap a central part of the sample plate 100. That is, air introduced into the aerosol collecting device 200 flows uniformly right and left. Under such configuration, particles absorbed onto the sample plate 100 are concentrated to a central part to the maximum. As the particles move toward an edge part of the sample plate 100, a concentrated degree is lowered.

Figure 4:
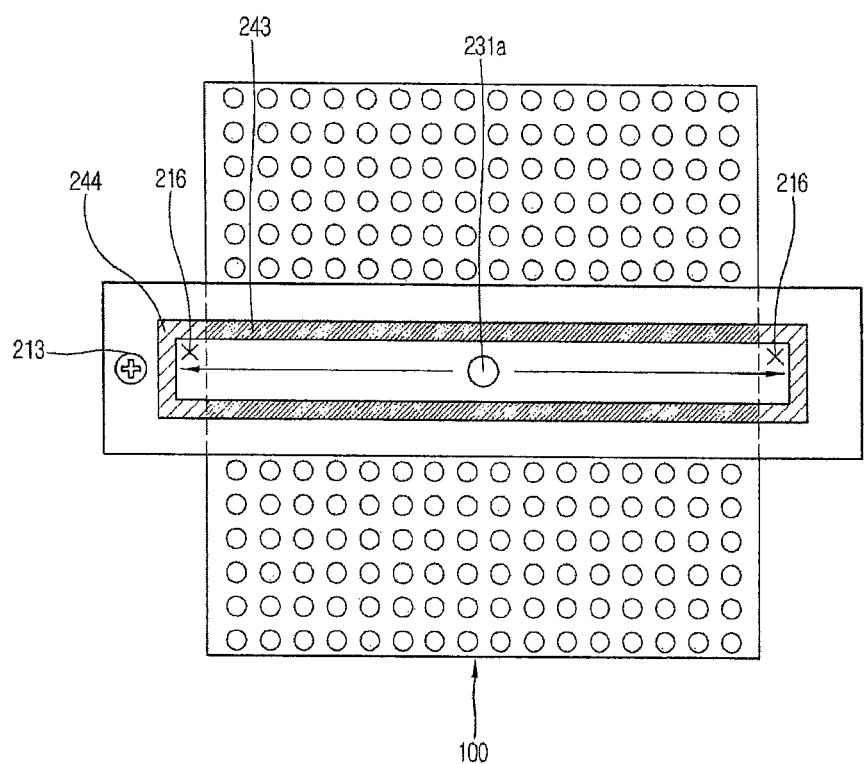
FIG. 4 is a planar view of the aerosol collecting device of FIG. 1.
Figure 5:
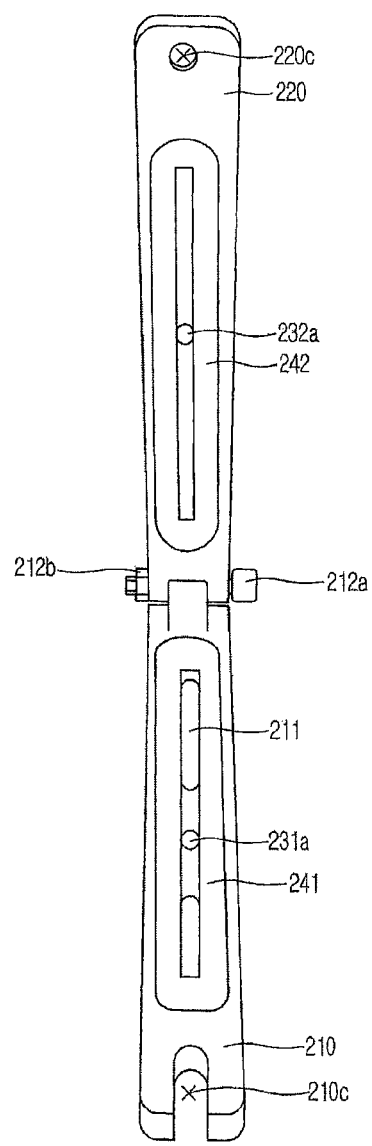
FIG. 5 is a view illustrating an inner configuration of the aerosol collecting device of FIG. 1.
Figure 6:
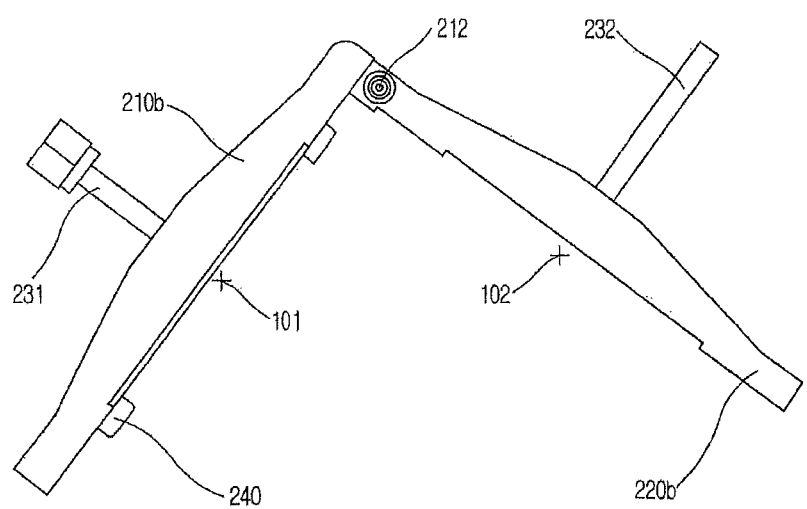
FIG. 6 is a side sectional view of the aerosol collecting device of FIG. 1.

FIG. 4 is a planar view of the aerosol collecting device 200 of FIG. 1, FIG. 5 is a view illustrating an inner configuration of the aerosol collecting device 200 of FIG. 1, and FIG. 6 is a side sectional view of the aerosol collecting device 200 of FIG. 1.

Referring to FIGS. 4 to 6, the contact member 240 includes a first member attached to an inner surface of the first body 210, and a second member attached to an inner surface of the second body 220.

The second member forms a sealed space by being engaged with the first member.

Referring to FIG. 5, the first member includes a first central region spaced from the sample plate 100 and forming a sample passing space, and a first edge part formed to enclose the first central region. The second member has a shape corresponding to the first member. That is, the second member includes a second central region spaced from the sample plate 100 and forming a sample passing space, and a second edge part formed to enclose the second central region.

In another embodiment of the present invention, the first member includes a first hole entirely covering an inner surface of the first body 210, and overlapping the sample inlet. The second member includes a second hole entirely covering an inner surface of the second body 220, and overlapping the suction opening.

When the housing is in a closed state, the first edge portion and the second edge portion are engaged with each other. As a result, air inside the aerosol collecting device 200 is not discharged to outside. However, when the first edge portion and the second edge portion have a width smaller than that of the sample plate 100, air inside the first body 210 does not flow into the second body 220.

Referring to FIG. 4, the contact member 240 has a width larger than that of the sample plate 100. That is, the first edge portion is divided into a first region 243 contacting the sample plate 100 by crossing the sample plate 100 in a width direction, and a second region 244 contacting the second edge portion. Likewise, the second edge portion is divided into a first region 243 contacting the sample plate 100 by crossing the sample plate 100 in a width direction, and a second region 244 contacting the first edge portion. That is, the first edge portion and the second edge portion partially contact the sample plate 100, and partially contact each other. Under such configuration, air inside the aerosol collecting device 200 is not discharged to outside.

A sample passing region 216 is formed between the second region 244 and the sample plate 100. As indicated by the arrows, air introduced to the aerosol collecting device 200 through the sample inlet is discharged to the suction opening, via the sample passing region 216 disposed at two sides of the sample plate 100 and an inner space of the second body 220.

Referring to FIG. 6, the aerosol collecting device includes a first body 210, a second body 220, a first connection member 231 protruding from the first body 210, a second connection member 232 protruding from the second body 220, etc.

The first body 210 and the second body 220 may be open and closed in a state where one end thereof is hinge-connected to each other by a fixing pin. FIGS. 5 and 6 illustrate an open state of the housing, and FIGS. 1 and 2 illustrate a closed state of the housing.

Referring to FIGS. 5 and 6, one end of the first body 210 is coupled to one end of the second body 220 by a fixing pin, thereby forming a fixing end. The fixing pin 212 is configured to bolt portion 212a and nut portion 212b. Reference numerals 241 and 242 denote a first edge portion (or part) 241 and second edge portion (or part) 242, respectively. Another ends of the first body 210 and the second body 220 form a free end. Bolt grooves 210c and 220c are formed at another ends of the first body 210 and the second body 220. As bolts are coupled to the bolt grooves 210c and 220c after the housing is closed, a closed state of the housing is maintained.

A threaded rod may be formed on an inner surface of the bolt groove 220c of the second body 220. After the housing is closed, a bolt where a screw thread has been formed is inserted into the bolt groove 220c, and then is rotated. As a result, the first body 210 and the second body 220 can be adhered to each other by a higher adhesive force.

A groove 101, having a shape corresponding to the sample plate 100, is formed on a side surface of the first body 210. Likewise, a groove 102, having a shape corresponding to the sample plate 100, is formed on a side surface of the second body 220. The grooves 101 and 102 serve to allow the first body 210 and the second body 220 to be engaged with each other therethrough, in a state where the sample plate 100 is interposed therebetween. That is, the sample plate 100 is fixed to the grooves 101 and 102.

Figure 7:
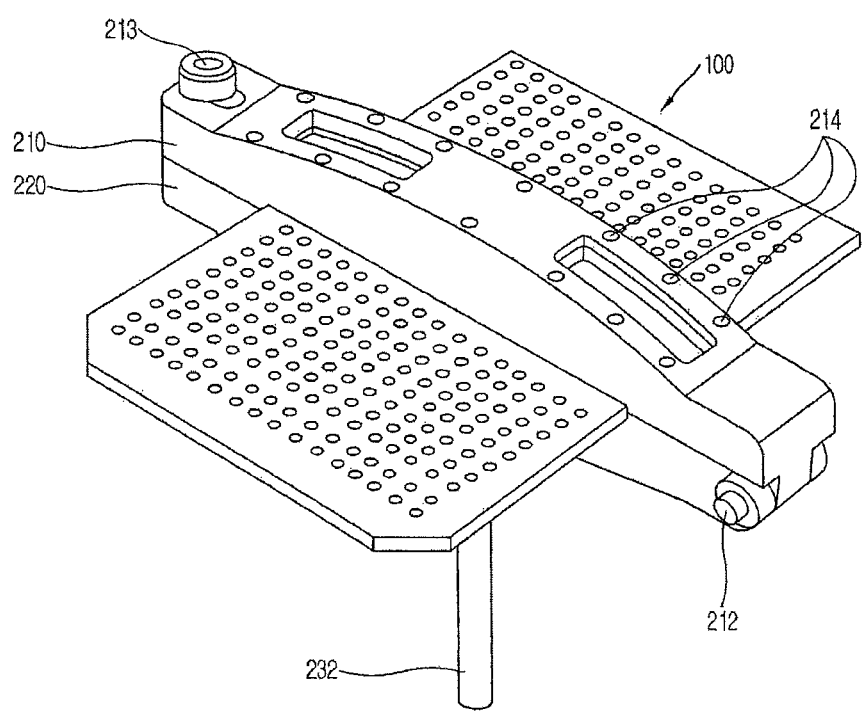
FIG. 7 is a perspective view of an aerosol collecting device according to another embodiment of the present invention.
Figure 8:
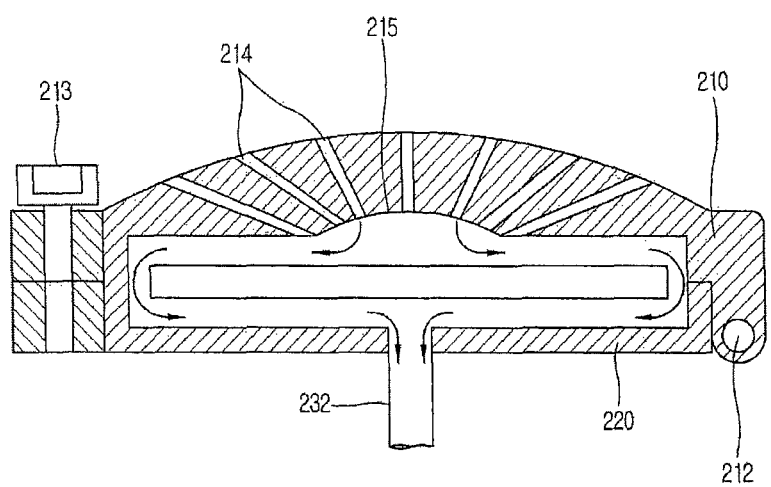
FIG. 8 is a sectional view of the aerosol collecting device of FIG. 7.

FIG. 7 is a perspective view of an aerosol collecting device 200 according to another embodiment of the present invention, and FIG. 8 is a sectional view of the aerosol collecting device 200 of FIG. 7.

Referring to FIGS. 7 and 8, a housing includes a first body 210 and a second body 220.

The first body 210 is formed to cover an upper surface of the sample plate 100, and the second body 220 is formed to cover a lower surface of the sample plate 100.

A concaved surface 215 is formed on an inner surface of the first body 210. The first body 210 includes a plurality of ports 214 connected from an outer surface of the first body 210 to the concaved surface.

A central space of the aerosol collecting device 200 is formed by the concaved surface, and particles introduced into the aerosol collecting device 200 through the ports 214 are collected to the central space. Then, the particles are dispersed to two sides of the sample plate 100. That is, air introduced into the aerosol collecting device 200 flows along the sample passing space formed around the sample plate 100, and is discharged to the suction opening. A flowing direction of the air is indicated by the arrows.

A pressure controller, configured to control an inner pressure of the sample passing space, may be connected to the suction opening. If an inner pressure of the aerosol collecting device 200 is lower than an atmospheric pressure, air is introduced into the aerosol collecting device 200 through the sample inlet. Aerosol particles in the air collide with an upper surface of the sample plate 100 due to inertia. Massive particles collide with the sample plate 100 to thus be absorbed onto the surface of the sample plate 100. On the other hand, light particles are introduced into the second body 220 through the sample passing space disposed at two sides of the sample plate 100, along a flowing direction of air. Then, the light particles are discharged to the suction opening.

In this embodiment, aerosol particles which exist around the aerosol collecting device 200 can be absorbed to the aerosol collecting device 200 in a more rapid and efficient manner, using the plurality of ports 214 of the housing.

Figure 9:
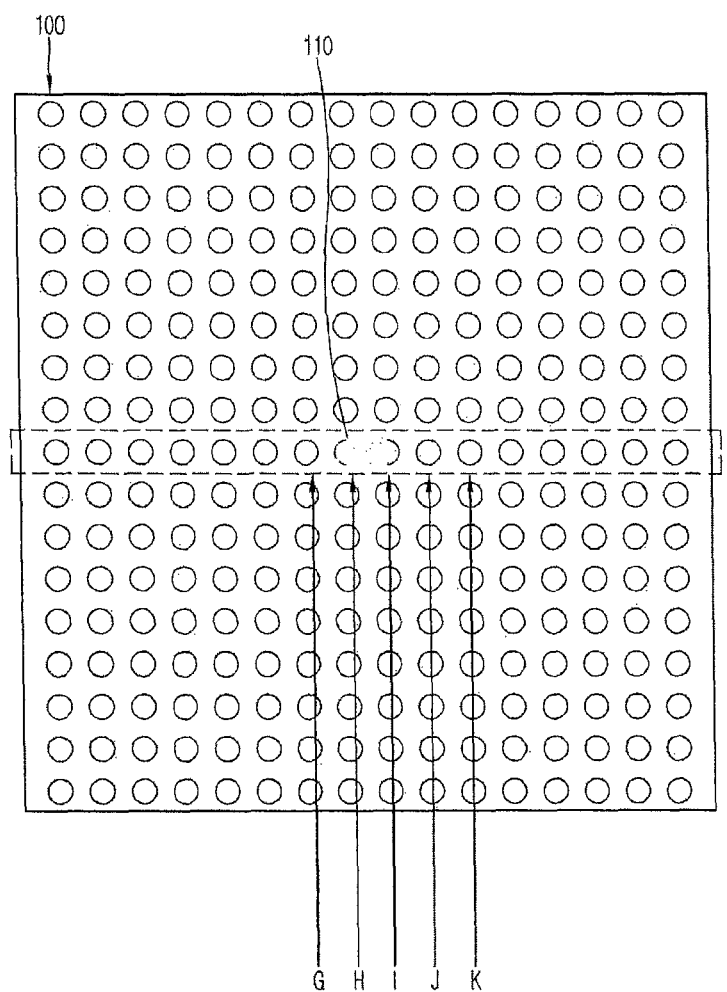
FIG. 9 is a conceptual view illustrating an operation to collect aerosols using an aerosol collecting device according to the present invention.
Figure 10:
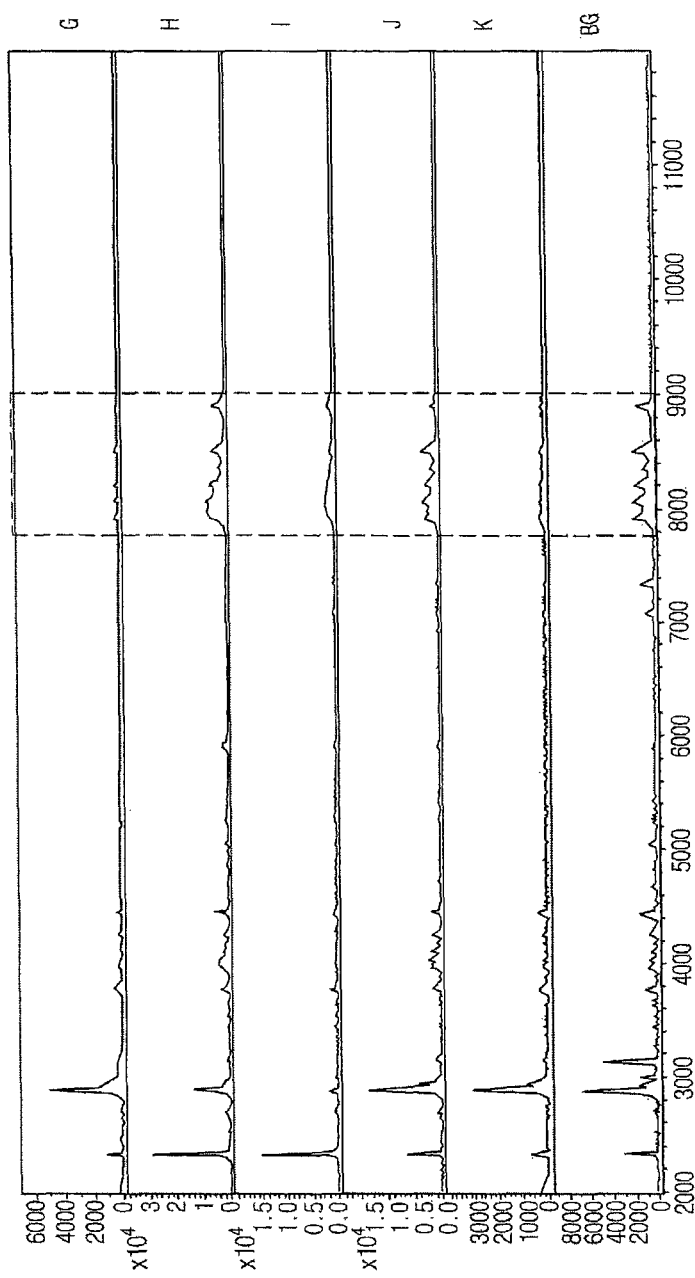
FIG. 10 is a view illustrating mass spectra of the aerosols of FIG. 9.

FIG. 9 is a conceptual view illustrating an operation to collect aerosol using the aerosol collecting device 200 according to the present invention, and FIG. 10 is a view illustrating mass spectra of the aerosols of FIG. 9.

FIGS. 9 and 10 illustrate experimental results on samples collected using the aerosol collecting device 200 according to the present invention. Firstly, bioaerosols were generated in the air using a bubble burst-type generator, and then the sample was collected using the aerosol collecting device 200 according to the present invention. As the bioaerosols, *bacillus* globiggi (hereinafter, will be referred to as 'BG') was used.

Conditions applied to experiments are as follows.

A pump is connected to the suction opening of the aerosol collecting device 200, so that BG aerosol in the air is introduced into the aerosol collecting device 200.

A BG suspension (concentration: $1 \times 10^{10}$ CFU/ml) is supplied to an aerosol generator with a speed of 71.26 a/min, thereby generating aerosol. Then, the aerosol is mixed with air filtered by a HEPA (High-efficiency Particulate Air) filter. The pump is connected to the suction opening connected to the second body 220, for suction of aerosol mixed with the air through the suction opening of the aerosol collecting device 200. The BG sample was collected with a speed of about 7 l/min for 5 minutes. A great amount of BG sample was collected on the sample plate 100 for 5 minutes.

Then, a matrix (HCCA: -cyano-4-hydroxycinnamic acid) was dropped onto to the BG collected onto the sample plate 100. Then, the matrix was dried at room temperature for several minutes, and then was analyzed using MALDI-TOF mass spectrometer (Autoflex Speed LRF mass spectrometer, Bruker Daltonics, Germany).

A mass spectrum shown in the lowest part of FIG. 10 is a mass analysis result on BG suspension 1. The mass analysis was performed by dropping the BG suspension 1 using a pipette. The above 5 spectra data shows mass spectra measured in dropping spots on columns G, H, I, J and K of FIG. 9. The dotted region indicates a region where a characteristic mass spectrum of the BG is shown.

Referring to FIG. 10, mass spectra measured with respect to samples collected onto dropping spots on columns G, H, I, J and K are consistent with mass spectra with respect to samples directly dropped from the BG suspension. This means that the aerosol collecting device according to the present invention does not have a difficulty in identifying BG aerosols directly collected from the air, without a sample concentration process and a sample dropping process which are generally performed in a laboratory.

The aerosol collecting device according to at least one embodiment of the present invention is configured to collect bioaerosols floating in the air by directly absorbing onto the MALDI-TOF sample plate 100. Accordingly, a sample concentration process and a sample dropping process can be omitted. Under such configuration, time taken to preprocess the sample can be reduced, and thus whether a biological attack has occurred or not can be early determined.

The foregoing embodiments and advantages are merely exemplary and are not to be considered as limiting the present disclosure. The present teachings can be readily applied to other types of apparatuses. This description is intended to be illustrative, and not to limit the scope of the claims. Many alternatives, modifications, and variations will be apparent to those skilled in the art. The features, structures, methods, and other characteristics of the exemplary embodiments described herein may be combined in various ways to obtain additional and/or alternative exemplary embodiments.

As the present features may be embodied in several forms without departing from the characteristics thereof, it should also be understood that the above-described embodiments are not limited by any of the details of the foregoing description, unless otherwise specified, but rather should be considered broadly within its scope as defined in the appended claims, and therefore all changes and modifications that fall within the metes and bounds of the claims, or equivalents of such metes and bounds are therefore intended to be embraced by the appended claims.

What is claimed is:

1. An aerosol collecting device, comprising:
    a sample plate; and
    a housing having a sample passing space around the sample plate so as to enclose at least part of the sample plate,
    wherein the housing includes:
    a first body having a sample inlet on one surface thereof;
    a second body having a suction opening on one surface thereof, the suction opening configured to suck air inside the sample passing space, the second body formed to be engaged with the first body in a state where the sample plate is interposed therebetween; and
    a first contact member mounted to a region so as to be adhered to an interface with the sample plate,
    wherein the first contact member includes:
    a first member attached to an inner surface of the first body, and
    a second member attached to an inner surface of the second body, and configured to seal the sample passing space by contacting the first member,
    wherein the first member includes:
    a first hole covering an inner surface of the first body, and surround the sample inlet;
    a first central portion spaced from the sample plate to form a sample passing space; and
    a first edge portion enclosing the first central portion, and formed to be engaged with the second member,
    wherein the second member includes:
    a second hole covering an inner surface of the second body, and surround the suction opening;
    a second central portion spaced from the sample plate to form a sample passing space; and
    a second edge portion enclosing the second central portion, and formed to be engaged with the first edge portion,
    wherein the first edge portion includes:
    a first region contacting the sample plate; and
    a second region contacting the second edge portion.

2. The aerosol collecting device of claim 1, wherein the sample inlet and the suction opening are disposed to face each other.

3. The aerosol collecting device of claim 1, wherein the first body includes:
    a first surface including the sample inlet; and
    a second surface extending from one end of the first surface in a thickness direction of the housing, and having a groove on one end thereof, the groove formed to have a shape corresponding to the sample plate.

4. The aerosol collecting device of claim 3, wherein the second body includes:
    a third surface including the suction opening; and
    a fourth surface extending from one end of the third surface in a thickness direction of the housing, and having a groove on one end thereof, the groove formed to have a shape corresponding to the sample plate.

5. The aerosol collecting device of claim 1, wherein the sample passing space is formed between the second region and the sample plate.

6. The aerosol collecting device of claim 1, wherein the housing includes a first connection member protruding from the first body to thus have a prolonged length, the first connection member including a flow path for connecting the sample inlet to outside.

7. The aerosol collecting device of claim 1, wherein a concaved surface is formed at an inner surface of the first body.

8. The aerosol collecting device of claim 7, wherein the sample inlet includes a plurality of holes connected from an outer surface of the first body to the concaved surface.

9. The aerosol collecting device of claim 1, wherein the sample plate is a sample plate of a Matrix Assisted Laser Desorption and Ionization Time-Of-Flight (MALDI-TOF) mass spectrometer.

10. The aerosol collecting device of claim 1, further comprising a pressure controller connected to the suction opening, and configured to control a pressure inside the sample passing space.

11. The aerosol collecting device of claim 1, wherein the housing is formed to have a length shorter than that of the sample plate.

12. The aerosol collecting device of claim 11, wherein the housing includes a transparent window through which the sample plate is capable of being viewed from the outside.

* * * * *

UNITED STATES PATENT AND TRADEMARK OFFICE
CERTIFICATE OF CORRECTION

| | |
|---|---|
| PATENT NO. | : 9,322,751 B2 |
| APPLICATION NO. | : 14/097439 |
| DATED | : April 26, 2016 |
| INVENTOR(S) | : Lee et al. |

It is certified that error appears in the above-identified patent and that said Letters Patent is hereby corrected as shown below:

On the title page item (73), should read --AGENCY FOR DEFENSE DEVELOPMENT, Daejeon (KR)--

Signed and Sealed this
Twenty-sixth Day of July, 2016

Michelle K. Lee
*Director of the United States Patent and Trademark Office*